(12) United States Patent
Stannard et al.

(10) Patent No.: US 6,797,767 B2
(45) Date of Patent: Sep. 28, 2004

(54) POLYMERIZABLE COMPOSITE MATERIAL

(75) Inventors: Jan G. Stannard, Hanover, MA (US); Kenneth J. Berk, Newton, MA (US)

(73) Assignee: Pulpdent Corporation, Watertown, MA (US)

( * ) Notice: Subject to any disclaimer, the term of this patent is extended or adjusted under 35 U.S.C. 154(b) by 0 days.

(21) Appl. No.: 10/336,255

(22) Filed: Jan. 3, 2003

(65) Prior Publication Data

US 2004/0132937 A1 Jul. 8, 2004

(51) Int. Cl.[7] ............................................... C08L 31/00
(52) U.S. Cl. ........................ 524/559; 524/444; 524/556; 526/230; 526/277; 526/301; 526/323.1
(58) Field of Search ................. 526/230, 277, 526/301, 323.1; 524/556, 559

(56) References Cited

U.S. PATENT DOCUMENTS

| | | | |
|---|---|---|---|
| 6,315,566 B1 | * 11/2001 | Shen et al. | 433/226 |
| 6,326,417 B1 | * 12/2001 | Jia | 523/116 |
| 6,500,004 B2 | * 12/2002 | Jensen et al. | 433/228.1 |
| 6,653,365 B2 | * 11/2003 | Jia | 523/109 |
| 2003/0083400 A1 | * 5/2003 | Jia | |

FOREIGN PATENT DOCUMENTS

| | | | |
|---|---|---|---|
| EP | 0 347 711 A2 | * | 12/1989 |
| EP | 1 190 695 A1 | * | 3/2002 |
| JP | 2001-122718 | * | 5/2001 |
| JP | 2002-161013 | * | 6/2002 |
| JP | 2002-265312 | * | 9/2002 |

* cited by examiner

Primary Examiner—Helen L. Pezzuto
(74) Attorney, Agent, or Firm—Kirkpatrick & Lockhart LLP

(57) ABSTRACT

This invention relates to a polymerizable composite material and method of making at least one multifunctional acid containing monomer having a concentration ranging from about 10% to about 85%, a non-reactive filler having a concentration ranging from about 1% to about 80%, a polymerization system having a concentration ranging from about 1.5% to about 15%, and water having a concentration ranging from about 0.1% to about 25%.

21 Claims, 1 Drawing Sheet

Table 1

| Example | B | U | H | T | D | H2O | E | A | CQ | NaF | Submicron Glass | Micron Glass | Compressive Strength, MPa (S.D.) | Bond to Composite, lb. (S.D.) |
|---|---|---|---|---|---|---|---|---|---|---|---|---|---|---|
| 1 | 48.32 | 5.49 | 2.75 | 3.84 | 1.28 | 0.37 | 0.27 | 0.51 | --- | 1.10 | 1.83 | 34.23 | 155(8) | --- |
| 2 | 43.19 | 4.91 | 2.45 | 2.29 | 1.14 | 0.33 | 0.24 | 0.46 | --- | 1.10 | 1.50 | 42.42 | 156(8) | --- |
| 3 | 41.72 | --- | --- | 2.21 | 1.11 | 4.93 | 0.24 | --- | 0.19 | --- | 1.60 | 48.02 | 120(4) | --- |
| 4 | 78.00 | 8.86 | --- | 4.13 | 2.07 | 4.87 | 0.44 | --- | 0.35 | 0.12 | 1.18 | --- | --- | 32(10) |
| 5 | 43.35 | 43.35 | --- | 4.13 | 2.06 | 5.00 | 0.44 | --- | 0.35 | 0.50 | 0.81 | --- | --- | 32(19) |
| 6 | 45.88 | 45.88 | --- | 4.37 | 2.18 | --- | 0.47 | --- | 0.37 | --- | 0.86 | --- | --- | 50(11) |
| 7 | 49.10 | 5.60 | 2.79 | 2.60 | 1.30 | 0.37 | 0.28 | --- | 0.22 | 1.11 | 1.86 | 34.78 | 141(16) | --- |
| 8 | 27.34 | 27.34 | 2.79 | 2.60 | 1.30 | 0.37 | 0.28 | --- | 0.22 | 1.11 | 1.86 | 34.78 | 204(27) | --- |
| 9 | 42.68 | 42.68 | 7.30* | 4.41 | 2.20 | --- | 0.47 | --- | 0.26 | --- | --- | --- | --- | 74(14) |
| 10A | 48.40 | 5.50 | 2.75 | 2.57 | 1.83 | 0.73 | 0.46** | --- | 0.37 | 1.10 | 1.83 | 34.28 | 350(2) | --- |
| 10B | --- | 55.10 | 2.81 | 2.62 | --- | --- | --- | --- | 1.40*** | 0.02 | 1.87 | 35.04 | --- | --- |
| 11 | 10.55 | 24.62 | 1.79 | 1.67 | 0.84 | 0.24 | 0.18 | --- | 0.12 | 1.10 | 2.00 | 56.90 | 260(20) | --- |
| 12 | 41.70 | 4.74 | 2.37 | 2.21 | 1.10 | 10.14 | 0.24 | --- | 0.19 | 0.95 | 1.87 | 34.48 | 71(4) | --- |
| 13 | 42.00 | 15.00 | --- | 2.60 | 2.00 | 15.00 | 0.28 | --- | 0.27 | 1.00 | 1.86 | 20.00 | 43(2) | --- |
| 14 | 42.68 | 32.56 | 5.00* | 4.41 | 2.20 | 5.00 | 0.47 | --- | 0.26 | 0.12 | --- | --- | --- | 51(9) |

\* 1,6 dihydroxy hexamethylene dimethacrylate
\*\* 1 acetyl-2-thio urea
\*\*\* cumene hydro peroxide B   Bis-2(methacryloxy)ethyl phosphate
U   diurethane dimethacrylate
H   hydroxyethylmethacrylate
T   tri-methyol propane tri-methacrylate
D   dimethyl amino ethyl methacrylate
H₂O water
E   ethyl 4 dimethylamino benzoate
A   acryl phosphine oxide
CQ  camphorquinone
NaF sodium fluoride

FIG. 1

POLYMERIZABLE COMPOSITE MATERIAL

FIELD OF THE INVENTION

This invention relates to polymerizable composite materials and, more particularly, polymerizable composite materials that are useful in restorative dental applications.

BACKGROUND OF THE INVENTION

Within the field of dentistry, a variety of materials are used to replace or assist in replacing missing tooth structure, including restorative materials and bonding agents (of ten referred to as adhesives). A restorative material typically replaces a portion of the tooth structure, whereas a bonding agent acts as a bond between the tooth structure and the restorative material. Due to their different uses, restorative materials and bonding agents may have different properties and qualities. For example, bonding agents need to have sufficient fluidity and often require the presence of a solvent such as water, acetone or alcohol to be effective. Typically, bonding agents lack filler materials or have filler levels less than 5% by weight. As such, bonding agents lack sufficient strength or aesthetics to be used as restorative materials in situations which require larger restorative quantities. Restorative materials need to have physical properties such as high compressive strength and low wear, and preferably have an acceptable aesthetic appearance, e.g., tooth-like appearance.

One type of dental material includes resin-reinforced glass ionomers. Glass ionomers require water for all or part of their curing or setting mechanism and require the mixing of two or more ingredients immediately prior to use. However, their uptake of water during setting, their subsequent expansion or contraction and their generally poor overall performance in terms of esthetic appearance have limited the use of glass ionomers as restorative materials. See, e.g., U.S. Pat. No. 5,264,513 to Kunio.

Another type of bonding agent or adhesive includes dental materials containing acidic monomers. Acidic monomers are polymerizable compounds that contain acid groups such as phosphoric, phosphonic, phosphinic, sulfuric, sulfonic or sulfinic moieties. Acidic monomers, such as phosphate esters, are known. Buonocore discussed such materials as early as 1956 in J. Dent. Res., 1956, pp. 846–851. In addition, solvent based materials containing phosphate esters were described in *Adhesive Restorative Dental Materials*, 1961, pp. 195–198. Typically, these materials contain high levels of volatile solvents and contain little or no inorganic filler material. See, e.g., U.S. Pat. No. 5,089,051 to Eppinger et al. and U.S. Pat. No. 6,245,872 to Frey et al. Generally, acidic monomers have not been previously used in combinations greater than 40% by weight due to the difficulty in polymerizing acidic monomers in high concentrations and/or the diminished physical properties obtained. See, e.g., U.S. Pat. No. 5,733,949 to Imazato et al.

A category of dental restorative materials includes resin-based composite materials. These composite materials typically contain both reactive monomers and nonreactive fillers. They are also typically hydrophobic in nature and do not bond well to tooth structure. A tooth itself may contain between 5–20% water and is present in an aqueous oral environment. Ion releasing resin-based restorative materials, including nonacidic monomers, are described in U.S. Pat. No. 6,180,688 to Rheinberger et al.

SUMMARY OF THE INVENTION

In general, in one aspect, the invention features a polymerizable composite material including at least one multifunctional acid containing monomer having a concentration ranging from about 10% to about 85%, a non-reactive filler having a concentration ranging from about 1% to about 80%, a polymerization system having a concentration ranging from about 1.5% to about 15%, and water having a concentration ranging from about 0.1% to about 25%.

In general, in another aspect, the invention features a method for making a polymerizable composite material. At least one multifunctional acidic monomer having a concentration ranging from about 10% to about 85% is provided. A non-reactive filler having a concentration ranging from about 1% to about 80% is added. A polymerization system having a concentration ranging from about 1.5% to about 15% is added. Water having a concentration ranging from about 0.1% to about 25% is further added.

An advantage of the present invention is that it provides restorative dental materials that are compatible with and are aesthetically acceptable in an oral environment. Additionally, one embodiment of the invention provides a polymerizable composite material that seals and protects a tooth while providing adequate strength to be used in restorative dental applications.

The details of one or more embodiments of the invention are set forth in the accompanying figure and the description below. Other features, objects, and advantages of the invention will be apparent from the description and figure, and from the claims.

FIGURE

FIG. 1 is a Table summarizing the components of the composite materials described in the examples provided herein.

DETAILED DESCRIPTION OF THE INVENTION

The present invention relates to polymerizable composite materials and methods of making such materials in which a strong, aesthetically acceptable dental restorative material is produced. The polymerizable composite material includes at least one multifunctional acidic monomer, a filler that does not react with the acidic monomer, a polymerization system, and may include water. The composite material may additionally contain other adjuncts to impart convenient handling characteristics and satisfy setting or curing requirements and other suitable qualities useful in restorative dentistry. For instance, the composite material may contain co-monomers to increase strength and reactivity of the material, water soluble salts such as sodium fluoride, and compounds to allow polymerization of the resin either by light curing or by auto polymerization.

The polymerization system typically includes initiators and accelerators which enable polymerization of the acid monomers when used in higher concentrations as well as in the presence of co-monomers.

The polymerization system of the present invention contains one or more amines in concentrations greater than those traditionally used in dental composite materials. It has been found that a combination of amines, in relatively high concentrations compared to the concentrations traditionally used in dental composite materials, created hard sets, sufficient for dental applications, in these materials in spite of the high levels of acidic monomers.

The co-monomers used further strengthen the acid integrating resin network and may be used to control water uptake, control surface characteristics such as the hydrophilic/hydrophobic nature of the materials, and increase the acidic monomer reactivity. The presence of sodium fluoride, which dissolves in water, may further enhance the sealing qualities of the material.

There appears to be a symbiotic relationship between the acidic monomers and the co-monomers. In addition to the feature described above, the co-monomer appears to have a higher level of conversion of its double bonds due to the acidic environment created by the acidic monomer.

These resin-based dental restorative compositions may integrate with tooth structure and other dental materials, do not require mixing (except where a dual cure material is described), are radiopaque, may release fluoride, and can be readily light cured on demand. They further have compressive strengths suitable for dental restorations,.and create a marginal seal of sufficient quality such that it is very difficult (and often not possible) to identify the margin of the material.

It has been found that by incorporating water into this material, the acidic groups become active as well as provide dissolved ionic compounds that enhance favorable tooth sealing (bonding). The dissolved ionic compounds also allow for the possibility of remineralization. The amount of water is important to optimize strength, reduce final water uptake, ionic solubilization and acid monomer activation. The selection of appropriate non-reactive fillers has been found to impart strength and cohesiveness to these materials allowing them to be used as restorative materials.

Co-monomers for this invention include but are not limited to polymerizable compounds such as diurethane dimethacrylate; hydroxyethylmethacrylate; trimethyol propane trimethacrylate; 1,6 dihydroxy hexamethyene dimethacrylate; triethylene glycol dimethacrylate; and bis glycidyl dimethacrylate (BIS-GMA).

Non-reactive fillers suitable for this invention are ones that will not react with the acid groups. In accordance with the acid strength of the monomers, suitable fillers include silica, barium aluminum silicate, silanated silica, alumina, quartz, radiopaque glass, and other materials well known to those skilled in the art.

The filler is made up of particles used to impart strength to the composite structure. The filler may contain particles of varying sizes. For example, the filler may include micron-sized or submicron-sized particles of silica ($SiO_2$). Micron-sized particles typically provide density, while submicron-sized particles typically act as a thickening and suspending agent. Further, the particles may be silanated, i.e., have a coating of silane. Although the filler material or particles do not react with the acidic monomer, the silane may react with the acidic monomer to enhance the strength of the composite material.

Polymerization accelerators for this invention include amine compounds such as N,N dimethyl amino-p-toluidine; dimethyl amino ethyl methacrylate, 4 ethyl dimethyl amino benzoate; and many other widely recognized accelerators. Sulfinic acid accelerators may also be used which include p-toluene sulfinic acid, and sodium salt. Other accelerators will be known to those skilled in the art.

Light curing compounds or photoinitiators include such compounds as camphorquinone, acylphosphine oxide, benzoin, and methyl benzil ether. Other photoinitiators will be known to those skilled in the art.

Two part, chemical cure formulas of this invention may require separation of polymerization accelerators from the initiator. Such an initiator may include benzoyl peroxide, cumene hydroperoxide, lauryl peroxide or any of a number of widely recognized peroxides for free radical or cationic/anionic polymerization reactions.

Water soluble salts include compounds such as sodium fluoride, stannous fluoride, iron fluoride, calcium fluoride and aluminum fluoride. Other appropriate water soluble salts will be known to those skilled in the art.

The following examples describe compositions of the invention in further detail. Examples are provided for different restorative dental applications. As such, the amount of filler added may vary greatly according to the strength necessary to resist mastication or provide sufficient fluidity of the material. The amount of the acidic monomer and co-monomer also may vary according to the hydrophilic nature of the tooth application. Additionally, the amount of water varies in order to control the extent of hydration. Because these materials generally contain water and are miscible with water, they are not affected by intra oral contamination with water.

The amount of filler varies from 1% to 80% by weight, depending on whether the material is used as a glaze suitable for sealing a margin of a restoration or for sealing a pre-carious resin, or as a highly filled, restorative material suitable for high strength, low wear applications such as Class I or Class II restorations. An intermediate filled material, in the range of 25–50% by weight, would be suitable for placement as a pit and fissure sealant, and as a Class I, Class III, Class IV or Class V restorative material.

The amount of the multifunctional acidic monomer may vary from 10–85% by weight of the material. In this fashion, greater amounts of acidic monomer may be provided for acid etching and tooth penetration of the resin prior to polymerization. Lower amounts of acidic monomer may be provided when greater filler content is required for additional strength in the final material.

The amount of water may vary from 0.0–80% to provide greater acidity and control of hydration.

The amount of the co-monomer may be varied from 5–80% to control the strength of the material through copolymerization, acid enhanced polymerization of the co-monomer, reaction of the acid monomer, and to impart some further hydrophilic or hydrophobic characteristics to the material. 2-hydroxyethyl methacrylate is an example of such a hydrophilic co-monomer. 1,6 dihydroxy hexamethylene dimethacrylate is an example of a hydrophobic co-monomer. The symbiotic relationship between the acidic monomer and the co-monomer has been described above.

A method of using the composite material includes providing the composite material, the composite material is applied to the tooth, and then is set or cured by activating the polymerization system such as by applying light to activate a light curing compound. For dual cure formulations, the materials are mixed together prior to application to the tooth.

To further illustrate the present invention, the following examples as summarized in the Table of FIG. 1 are provided, but the present invention is not to be construed as being limited thereto. Unless otherwise indicated, all percentages are by weight. The following symbols and definitions are used in the Table to represent the various components of the composite materials described in the examples:

B Bis-2(methacryloxy)ethyl phosphate (acidic monomer)
U diurethane dimethacrylate
H hydroxyethylmethacrylate
T tri-methyol propane tri-methacrylate
D dimethyl amino ethyl methacrylate
$H_2O$ water E ethyl 4 dimethylamino benzoate
A acryl phosphine oxide
CQ camphorquinone
NaF sodium fluoride In the examples, the compressive strength was determined using specimens molded in Delrin™ (6 mm×4 mm diameter) split thickness molds. Using an Instron mechanical testing instrument, the samples were evaluated at a crosshead speed of 0.5 in/min. All specimens were stored in water at 37° C. for 24 hours prior to testing. Compressive strength values reported are for the mean, plus or minus a standard deviation indicated in parentheses.

Interfacial bond strength was measured by bonding the test material to a composite specimen made from a commercially available material known as Flows-Rite, available from Pulpdent Corporation, Watertown, Mass. The composite specimens were made using the above described 6 mm×4 mm mold. The test material was bonded to the circular interface of the composite specimen. Using a three-point bonding apparatus, the interface between the composite specimen and test material was loaded to the breaking point. This value is reported as the interfacial bond strength.

Fluoride release was measured from 25 mm×1 mm thick discs made of the test material. Two such discs were each measured separately. After curing, the discs were suspended in plastic containers containing 25.0 ml distilled water. Fluoride ion concentration was measured using a fluoride ion specific electrode (available from Orion Research) and calibrated using fluoride ion standard solutions with TISAB buffer solution (available from Orion Research).

Sealing of a tooth was measured by using the material as a pit and fissure material. Ten teeth were sealed in this manner. Phosphoric acid was used to etch the tooth surface prior to material placement, as is customary for this application. The teeth were thermocycled for 1500 times between 5° to 55° C. to challenge the tooth/material interface. After thermocycling, the teeth were exposed to a silver nitrate solution for 2 hours to allow dye penetrate into any open margin areas. After dye penetration, the teeth were completely sealed, and then sectioned from 3–5 times per tooth. The amount of dye penetration and extent material penetration into the tooth was then measured.

All of the following examples have excellent tooth integrating properties and set within a clinically appropriate time to a hard mass.

EXAMPLES

Example 1

Example 1 has 48.3% acidic monomer with 36.0% filler, 0.37% water, and 1.1% sodium fluoride. This material has good compressive strength of 22, 400 (1200) psi or 155 (8) MPa., is moderately filled, has good fluidity, and is suitable as a pit and fissure sealant material. The material releases fluoride and sets to a hard mass when cured by a dental light curing unit within 10–15 seconds.

Example 2

Example 2 has 43.2% acidic monomer with 45.0% filler, 0.33% water, and 1.1% sodium fluoride. This material is more highly filled than Example 1 and has less fluidity. The material releases fluoride and cures within 10–15 seconds with a dental curing light.

Example 3

Example 3 has 42% acidic monomer with 49.6% filler, 4.9% water, no co-monomer and no sodium fluoride. The polymerization system (including camphorquinone as a light receptor and amines) sets to a hard mass within 10–15 seconds using a dental curing light. This material is more highly filled, and with nearly 5% water still has acceptable compressive strength as a dental cement.

Example 4

Example 4 has 78% acidic monomer, with only submicron filler, and 4.9% water. This material releases fluoride and is cured by the polymerization system to a hard, clear mass within 10–15 seconds. This material has tooth integrating properties, provides a good seal and bonds very well to other composite materials. It also has properties beneficial as a composite sealant or tooth glaze material.

Example 5

Example 5 has 43% acidic monomer with only submicron filler and 5.0% water. This material contains 0.5% sodium fluoride, and releases fluoride. This material also has good bonding properties to the composite. The material sets to a hard, clear mass using a dental curing light within 10–15 seconds. This material is also suitable as a composite sealant or tooth glaze.

Example 6

Example 6 has 46% acidic monomer with only submicron filler. This material contains no added water and no added sodium fluoride. With greater than 40% acidic monomer the material sets to a hard, clear mass using a dental curing light. This material does not release fluoride. However, as a composite sealant or glaze, the material possesses good interfacial bonding.

Example 7

Example 7 has 49% acidic monomer with 36.6% filler. This material releases fluoride and with a moderate level of filling has a compressive strength suitable as a dental cement or base/liner material. This material polymerizes using the polymerization system.

Example 8

Example 8 has 27.3% acidic monomer with 36.6% filler. This material releases fluoride and, with a moderate level of filler, has a compressive strength suitable for a pit and fissure sealant material. This material polymerizes using the polymerization system.

This material, as an example of a pit and fissure sealant, was evaluated for its sealing ability of a tooth. Of all tooth surfaces evaluated, 65% of these showed no dye penetration at all. 35% of the surfaces showed dye penetration to the outer edge only, with no dye penetrating into the fissure itself. No surfaces had dye penetration to the bottom of the fissure. With respect to material penetration into the fissure, this material flowed easily to the extent of the fissure. These results indicate both excellent sealing and protection of the tooth from fluid penetration.

Example 9

Example 9 was 42.7% acidic monomer with no filler. 1,6 dihydroxy hexamethylene dimethacrylate, is substituted for hydroxyethylmethacrylate to provide more hydrophobic character to the material.

Example 10

Example 10 is a two-part composition which is dual cure (can be cured by light or left to autopolymerize after mixing, or both). Part A and Part B are mixed in equal parts. The mix can be light cured upon demand. The autopolymerization can be controlled; in this example, it starts at 4:30 minutes and is completed by 10:00 minutes. Part A has 48.4% acidic monomer, 37.2% filler and contains both sodium fluoride (1.10%) and water (0.73%). In Part A, 1 acetyl-2-thio urea was substituted for ethyl 4 dimethylamino benzoate, and in Part B, cumene hydro peroxide was substituted for camphorquinone. The material sets to a very strong, hard mass in either self cure or light cure mode. The material has very good retentive properties with respect to metal ceramic as well as tooth structure.

Example 11

Example 11 is a more highly filled material. The filler percentage is 60.0%, with 1.10% sodium fluoride and 0.24% water. The acidic monomer percentage is 10.55% overall, or 28.54% relative to only the primary monomers. The material is strong, as indicated by a compressive strength of 260 (20) MPa.

Example 12

Example 12 has 41.7% acidic monomer, 10.14% water and 37.3% filled. The material sets within 10–15 seconds to a hard mass with a dental curing light. The material has a compressive strength of 71 (4) MPa. The material may be used as a dentin replacement material or as a base/liner within a restoration.

Example 13

Example 13 has 42% acidic monomer, 15% water and 22.85% filler. This material contains NaF and releases fluoride ions. The material has a compressive strength of 43 (2) MPa.

Example 14

Example 14 has 42.68% acidic monomer, 5% water and contains only sodium fluoride, with no undissolvable filler. The material contains 5.00% 1,6 dihydroxy hexamethylene dimethacrylate instead of hydroxyethlymethocrylate. This material may be used as a glaze. It releases fluoride.

Various modifications and alterations of this invention will be apparent to those skilled in the art without departing from the scope and spirit of this invention. This invention should not be restricted to that set forth herein for illustrative purposes only.

What is claimed is:

1. A polymerizable composite material comprising:
   at least one multifunctional acid containing monomer having a concentration ranging from about 10% to about 85% by weight;
   a non-reactive filler having a concentration ranging from about 1% to about 80% by weight;
   a polymerization system capable of being activated by light to polymerize the composite material, the polymerization system having a concentration ranging from about 1.1% to about 15% by weight and comprising a photoinitiator and an accelerator, the accelerator having a concentration ranging from about 1.0% to about 15% by weight; and
   water having a concentration ranging from about 0.1% to about 25% by weight.

2. The polymerizable composite material of claim 1 wherein the multifunctional acidic monomer is bis-2 (methacryloxy)ethyl phosphate.

3. The polymerizable composite material of claim 1 further comprising a non-acid co-monomer having a concentration ranging from about 5% to about 80% by weight.

4. The polymerizable composite material of claim 3 wherein the non-acid co-monomer is diurethane dimethacrylate, hydroxyethylmethacrylate, trimethyol propane trimethacrylate, 1,6 dihydroxy hexamethyene dimethacrylate, triethylene glycol dimethacrylate, bis glycidyl dimethacrylate, or a combination thereof.

5. The polymerizable composite material of claim 1 wherein the non-reactive filler is silica, radiopaque glass, barium aluminum silicate, silanated silica, alumina, quartz, or a combination thereof.

6. The polymerizable composite material of claim 1 wherein the photoinitiator is camphorquinone, acylphosphine oxide, benzoin, methyl benzil ether or a combination thereof.

7. The polymerizable composite material of claim 1 further comprising an ionic compound having a concentration ranging from about 0.01% to about 10% by weight.

8. The polymerizable composite material of claim 7 wherein the ionic compound is sodium fluoride, stannous fluoride, iron fluoride, calcium fluoride, aluminum fluoride or a combination thereof.

9. A polymerizable composite material comprising:
   at least one multifunctional acid containing monomer having a concentration ranging from about 40% to about 85% by weight;
   a non-reactive filler having a concentration ranging from about 1% to about 80% by weight; and
   a polymerization system capable of being activated by light to polymerize the composite material, the polymerization system having a concentration ranging from about 1.1 to about 15% by weight and comprising a photoinitiator and an accelerator, the accelerator having a concentration ranging from about 1.0% to about 15% by weight.

10. The polymerizable composite material of claim 9 further comprising water having a concentration ranging from about 0.1% to about 25% by weight.

11. A method of making a polymerizable composite material comprising:
   providing at least one multifunctional acid containing monomer having a concentration ranging from about 10% to about 85% by weight;
   adding a non-reactive filler having a concentration ranging from about 1% to about 80% by weight;
   adding a polymerization system capable of being activated by light to polymerize the composite material, the polymerization system having a concentration ranging from about 1.1% to about 15% by weight and comprising a photoinitiator and an accelerator, the accelerator having a concentration ranging from about 1.0% to about 15% by weight; and
   adding water having a concentration ranging from about 0.1% to about 25% by weight.

12. The polymerizable composite material of claim 1, wherein the polymerization system concentration ranges from about 1.5% to about 15% by weight.

13. The polymerizable composite material of claim 1, wherein the accelerator is N,N dimethyl amino-p-toluidine, dimethyl amino ethyl methacrylate, 4 ethyl dimethyl amino benzoate, or a combination thereof.

14. The polymerizable composite material of claim 1, wherein the polymerization system is capable of dual curing to polymerize the composite material.

15. The polymerizable composite material of claim 9, wherein the polymerization system concentration ranges from about 1.5% to about 15% by weight.

16. The polymerizable composite material of claim 9, wherein the polymerization system is capable of dual curing to polymerize the composite material.

17. The method of making a polymerizable composite material of claim 11, wherein the polymerization system concentration ranges from about 1.5% to about 15% by weight.

18. The method of making a polymerizable composite material of claim 11, wherein the polymerization system is capable of dual curing to polymerize the composite material.

19. A polymerizable composite material comprising:

at least one multifunctional acid containing monomer having a concentration ranging from about 10% to about 85% by weight;

a non-reactive filler having a concentration ranging from about 1% to about 80% by weight;

a polymerization system capable of being activated only by light to polymerize the composite material, the polymerization system having a concentration ranging from about 1.1% to about 15% by weight and comprising a photoinitiator and an accelerator, the accelerator having a concentration ranging from about 1.0% to about 15% by weight; and water having a concentration ranging from about 0.1% to about 25% by weight.

20. A polymerizable composite material comprising:

at least one multifunctional acid containing monomer having a concentration ranging from about 40% to about 85% by weight;

a non-reactive filler having a concentration ranging from about 1% to about 80% by weight; and a polymerization system capable of being activated only by light to polymerize the composite material, the polymerization system having a concentration ranging from about 1.1% to about 15% by weight and comprising a photoinitiator and an accelerator, the accelerator having a concentration ranging from about 1.0% to about 15% by weight.

21. A method of making a polymerizable composite material comprising:

providing at least one multifunctional acid containing monomer having a concentration ranging from about 10% to about 85% by weight;

adding a non-reactive filler having a concentration ranging from about 1% to about 80% by weight;

adding a polymerization system capable of being activated only by light to polymerize the composite material, the polymerization system having a concentration ranging from about 1.1% to about 15% by weight and comprising a photoinitiator and an accelerator, the accelerator having a concentration ranging from about 1.0% to about 15% by weight; and adding water having a concentration ranging from about 0.1% to about 25% by weight.

* * * * *

UNITED STATES PATENT AND TRADEMARK OFFICE
CERTIFICATE OF CORRECTION

PATENT NO. : 6,797,767 B2
DATED : September 28, 2004
INVENTOR(S) : Stannard et al.

It is certified that error appears in the above-identified patent and that said Letters Patent is hereby corrected as shown below:

Drawings,
Fig. 1, the term "Bis-2(methacryloxy)ethyl" should be changed to
-- Bis-2(methacryloyloxy)ethyl --.

Column 4,
Line 61, the term "Bis-2(methacryloxy)ethyl" should be changed to
-- Bis-2(methacryloyloxy)ethyl --.

Column 7,
Lines 66-67, the term "bis-2(methacryloxy)ethyl" should be changed to
-- bis-2(methacryloyloxy)ethyl --.

Signed and Sealed this

Twelfth Day of April, 2005

JON W. DUDAS
*Director of the United States Patent and Trademark Office*